US006480186B1

(12) United States Patent
McCabe et al.

(10) Patent No.: US 6,480,186 B1
(45) Date of Patent: Nov. 12, 2002

(54) APPARATUS AND METHOD FOR INVOKING AN ANNOTATION FUNCTION FOR AN ULTRASOUND MACHINE

(75) Inventors: Laurence S. McCabe, Sunnyvale, CA (US); Janice Wojciechowski, Mountain View, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/174,190

(22) Filed: Oct. 16, 1998

(51) Int. Cl.$^7$ .................................................. G09G 5/00
(52) U.S. Cl. ...................................... 345/168; 600/437
(58) Field of Search ....................... 345/168; 128/653.1, 128/630, 697; 600/510, 523, 427, 437

(56) References Cited

U.S. PATENT DOCUMENTS

| | | | |
|---|---|---|---|
| 4,599,611 A | | 7/1986 | Bowker et al. |
| 4,833,625 A | * | 5/1989 | Fisher et al. ................. 364/518 |
| 5,315,999 A | * | 5/1994 | Kinicki et al. .......... 128/660.07 |
| 5,553,620 A | | 9/1996 | Snider et al. |
| 5,625,833 A | * | 4/1997 | Levine et al. ................ 395/800 |
| 5,680,636 A | * | 10/1997 | Levine et al. ................ 395/800 |
| 5,724,985 A | * | 3/1998 | Snell et al. ................... 128/697 |
| 5,740,801 A | * | 4/1998 | Branson .................... 128/653.1 |
| 5,795,297 A | * | 8/1998 | Daigle .......................... 600/447 |
| 6,063,030 A | * | 5/2000 | Vara et al. .................... 600/437 |
| 6,115,626 A | * | 9/2000 | Whayne et al. .............. 600/427 |
| 6,149,587 A | * | 10/2000 | Raines ......................... 600/300 |
| 2001/0035866 A1 | * | 11/2001 | Finger et al. ................ 345/568 |

OTHER PUBLICATIONS

Acuson Corporation, Copyright 1998, Acuson Home Page, web site page, <www.acuson.com>, pp. 1.
Hewlett Packard Company, Copyright 1994–1998, HP in Healthcare—HP SONOS 2500, web site, <www.hp.com/mpg/services/partners/unit 335.html>, pp. 1.
Philips Electronics N.V., Copyright 1998, SD 800 Ultrasound's advanced value platform, web site, <www.medical.philips.com/products/ultra/sd800.htm>, pp. 1–2.
ATL Corporation, unknown, Taking Ultrasound to a Higher Level, web site page, <www.atl.com/prod/r1715va–3.html>, pp. 1–3.
Hylton B. Meire and Pat Farrant, Sep. 1995, Basic Ultrasound, Book, John Wiley & Sons, Ltd.; West Sussex, England, pp. 1–7, 20–55, 204–213.

* cited by examiner

*Primary Examiner*—Amare Mengistu

(57) ABSTRACT

A method and apparatus is provided for annotating an image captured by an ultrasound system, which has an input device with a plurality of console keys for receiving input from an operator. The plurality of console keys includes an alphanumeric input device, such as a keyboard, used for placing characters on the image. An annotation function is invoked by pressing a key of the alphanumeric input device. The annotation function is for placing a character on the image in response to a character code from the alphanumeric input device. In a further aspect of the invention, the input device is provided with a pointing device, such as a track ball, which is spaced apart from the alphanumeric input device such that unintentional invocation of the annotation function is minimized. According to the method of the present invention, a key of the alphanumeric input device is pressed. In response to a character code generated by pressing the key, the annotation function is invoked. Subsequent pressing of a key on the alphanumeric input device generates subsequent character codes, which are placed on the image displayed by the ultrasound system.

20 Claims, 2 Drawing Sheets

## APPARATUS AND METHOD FOR INVOKING AN ANNOTATION FUNCTION FOR AN ULTRASOUND MACHINE

TECHNICAL FIELD

The present invention relates generally to ultrasound systems, and in particular to invoking annotations functions on ultrasound systems with increased efficiency, and with minimized probability of unintentional invocation of the annotation function.

BACKGROUND OF THE INVENTION

Generally, overlaid text or bitmap images can be added to a graphics display image on a computer monitor. These overlaid images provide additional information that is input by an operator. This information is commonly in the form of annotations that are added to more clearly convey information that pertains to the image.

In ultrasound systems, monitors are used as the final edit device for images captured with an ultrasound scanner. These scanners are devices used by an operator to produce images of anatomical objects on a monitor screen based on the absorption and reflection of high frequency sound waves. The operator places the ultrasound scanner or transducer over the area of interest, and by manipulating the scanner obtains an optimal view of the relevant anatomy or pathology of a patient. Present day scanners provide a real-time image to the monitor that is a relatively continuous display of tissue movements beneath the scanner. To achieve this end, the ultrasound beam must be scanned rapidly and repeatedly through the imaging plane by either mechanical or electronic means.

Streaming video to the ultrasound monitor screen is considered one operation mode for the ultrasound scanner. Another operation mode for present day scanning devices has been the "capturing" of the real-time images for record purposes. Typically, these captured images are recorded either digitally or on paper for later reference or to capture the instances of an abnormality identified within the patient. These images, when recorded, are typically required to be stored in a retrievable format for several years. Furthermore, when the images are captured on the monitor, the ultrasound operator has the option of entering into an annotation mode through the input devices attached to the ultrasound system.

A typical input device is composed of a series of control buttons on a control panel that are used to cause the ultrasound scanner components to enter into different operational functions. For example, as mentioned briefly above, there is a video streaming mode in which real-time video is conveyed from the images scanned by the scanner and placed onto the ultrasound monitor. Another mode is the capture mode, as also mentioned above. A further operational mode is image annotation.

Familiarity with the several functions of the ultrasound system typically requires a fairly lengthy learning process by operators unfamiliar with the layout and capabilities of the equipment. Compounding the complexity of these devices is the inefficient placement of the system command keys for an operator's convenience.

For example, existing ultrasound systems have used a specialized, relatively small, dedicated key—separate from the text keyboard—to invoke the annotation function. Several problems have arisen with this arrangement. First, an operator has to be well acquainted with a particular system to efficiently use the unit in the most expedient manner. This task is further complicated because an ultrasound system is used in a darkened room, typically having required an operator to locate this miniscule key by "feel." Second, the dedicated key requires an additional hand motion to invoke the annotation function, having resulted in additional inefficiencies in operating the ultrasound system.

Efficiency is a prime consideration because in the present medical environment, time and budget constraints have taken a prime importance with respect to the practice of medicine. Any efficiencies diminished by the lack of familiarity by the operator, or the inefficient or non-ergonomic design of a piece of medical equipment easily translates into time overruns and, accordingly, cost overruns with respect to the medical facility operating the machinery.

In this regard, more efficient control panel layouts have been sought in which annotation functions are also invoked by pressing a key on the alphanumeric keyboards.

These systems, however, have not fully addressed ergonomic considerations with respect to the needs of the operator. For example, invoking the annotation functions in this way simultaneously embeds a character on the monitor image. That is, when the annotation function is not active, an on-screen cursor is not displayed on the monitor. Because the cursor has not been displayed before the key was pressed, a user would have no feedback to indicate where the character will appear on the monitor with respect to the displayed image.

Also, ultrasound systems have used standard alphanumeric keyboards for the annotation function. As a result, no particular designation is made on the keyboard indicating how the annotation function can be invoked. A user has to have been well trained and that the training have been reinforced to the particular ultrasound system. Otherwise, a person unfamiliar with such systems has been at a loss of how to efficiently operate the system.

Accordingly, a need presently exists for an ultrasound system that is more user-intuitive as to the application of annotation functions, which place graphical and textual characters on an image captured by an ultrasound system. Furthermore, needed is an annotation function that is considerate of an operator's use of the ultrasound console functions.

SUMMARY OF THE INVENTION

In accordance with the present invention, a method and apparatus is provided for annotating an image captured by an ultrasound system, which has an input device with a plurality of console keys for receiving input from an operator. The plurality of console keys includes an alphanumeric input device, such as a keyboard, used for placing characters on the image. An annotation function is invoked by pressing a key of the alphanumeric input device. The annotation function is for placing a character on the image in response to a character code from the alphanumeric input device. Another aspect of the invention is that the key pressed to invoke the annotation function is the space bar key of a QWERTY keyboard. In a further aspect of the invention, the input device is provided with a pointing device, such as a track ball, which is spaced apart from the alphanumeric input device such that unintentional invocation of the annotation function is minimized. In another aspect of the invention, the spatial relationship between the pointing device and the alphanumeric input device facilitates user-intuitive operation of the ultrasound system.

According to the method of the present invention, a key of the alphanumeric input device is pressed. In response to a character code generated by pressing the key, the annotation function is invoked. Subsequent pressing of a key on the alphanumeric input device generates subsequent character codes, which are placed on the image displayed by the ultrasound system.

BRIEF DESCRIPTION OF THE DRAWINGS

The accompanying drawings are incorporated into and form a part of the specification to illustrate examples of the present invention. These drawings together with the description serve to explain the principles of the inventions. The drawings are only included for purposes of illustrating preferred and alternative examples of how the inventions can be made and used and are not to be construed as limiting the inventions to only the illustrated and described examples. Various advantages and features of the present inventions will be apparent from a consideration of the drawings in which.

DETAILED DESCRIPTION

The principles of the present invention and advantages are best understood by referring to the illustrated embodiment depicted in the FIGURES, in which like reference numbers describe like parts.

Figure 1:
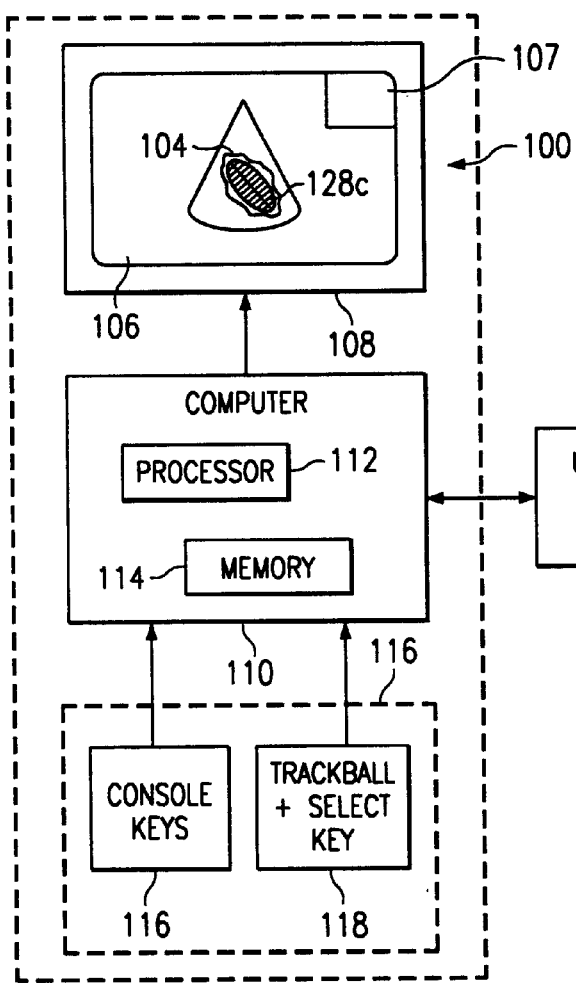
FIG. 1 is a diagram of an ultrasound system connected to an ultrasound imaging system.

FIG. 1 is a diagram of an ultrasound system 100 connected to the ultrasound imaging system 102. The ultrasound imaging system 102 acquires and presents an ultrasound image 104 that is displayed on the screen 106 of the monitor 108.

The image 104 can be a video stream mode in which real-time video is conveyed from the imaging system 102 and presented onto the ultrasound monitor 108. The operator may freeze these real-time images as they appear on the screen 106 so that a particular image 104 can be further analyzed. If an abnormality is found or a condition requiring generation of a record, the operator can then electronically store the image 104 for the patient records.

The monitor 108 is, preferably, a high-quality monitor, such as that commercially available from the Barco Inc. of Kennesaw, Ga. The imaging system 102 and the ultrasound system 100 are controlled by a microprocessor-based computer 110. Preferably, the computer 110 has a resident system control software process stored in the computer memory 114. In a preferred embodiment, the computer memory 114 includes a hard disk drive, a program memory, and a random-access-memory ("RAM"). The resident system control software process includes an operating system, such as the UNIX-based operating system, and a graphics system, such as the X-windows graphics server (a standardized set of display-handling routines developed for UNIX-based operating systems that allow the creation of hardware independent graphical user interfaces ("GUI")).

The graphics system is loaded into the program memory and RAM for execution by the microprocessor 112 of the computer 110 to control the images 104 displayed on the monitor 108. Microprocessor 112 is suitably powerful to execute the resident system control software process in conjunction with additional hardware such as display driver hardware, and the ultrasound imaging system 102 such that a sufficiently responsive operator interface is obtained. "Responsiveness" is somewhat subjective, but most developers are familiar with sources of guidelines, such as the Human Factors Society and the Association for Computer Human Interaction. In this regard, a preferred microprocessor is an Intel 586-series operating at 400 MHz. Other manufacturers of this microprocessor series are AMD, Inc., of Sunnyvale, Calif., and Cyrix Corporation of Richardson, Tex. It should be noted, however, that other processors can be implemented with satisfactory results, such as the Intel 486-series. It should be noted that other advanced microprocessor-based systems can be implemented as the computational power and speed of microprocessor technology advances.

An input device 116 includes a pointing device 118, with select keys 118a and 118b, and a plurality of console keys 120. The functional description of the console keys 120 is provided by a console template 123, which can be provided in variety of languages for accommodating users in different countries. Preferably the pointing device 118 is a trackball, which has a ball resting on two rollers at right angles to each other that translate the ball motion into vertical and horizontal movement of a cursor on the screen 106. This movement guides the on-screen cursor for such actions as "pressing" on-screen buttons in dialog boxes, choosing menu items 107, creating drawings or graphical shapes, or taking measurements of the images captured by the ultrasound imaging system 102. Measuring aspects of a captured image is discussed in further detail in U.S. Pat. No. 5,553,620, issued Sep. 10, 1996, to Snider et al. The select keys 118a and 118b are used to initiate other actions. A trackball is preferable for "fine" work because the operator can exert fingertip control, which is necessary in the operation of ultrasound equipment.

The console keys 120 allow input from an operator to initiate functions used in the ultrasound system 100, such as measurements, graphics adjustment, image annotations, or the like. Also, adjacent the pointing device 118 is a control key set 121 for commonly used ultrasound functions. This control key set 121 has a "VCR Record" key 121a, a "Clip Store" key 121b, an "Image Store" key 121c, a "Freeze/Run" wheel 121d, a "Cine" key 121e, a "Print" key 121f, and an "Aegis Review" key 121g. Those skilled in the art are familiar with the core functions of conventional ultrasound systems, and accordingly, are not discussed further herein. The aspect being emphasized with the present invention is the placement of the keys in a manner that is helpful to the user. Other possible input devices for the ultrasound system include voice recognition systems, touch screen systems, and any other way to control program menus and images displayed on the monitor screen 106.

Figure 2:
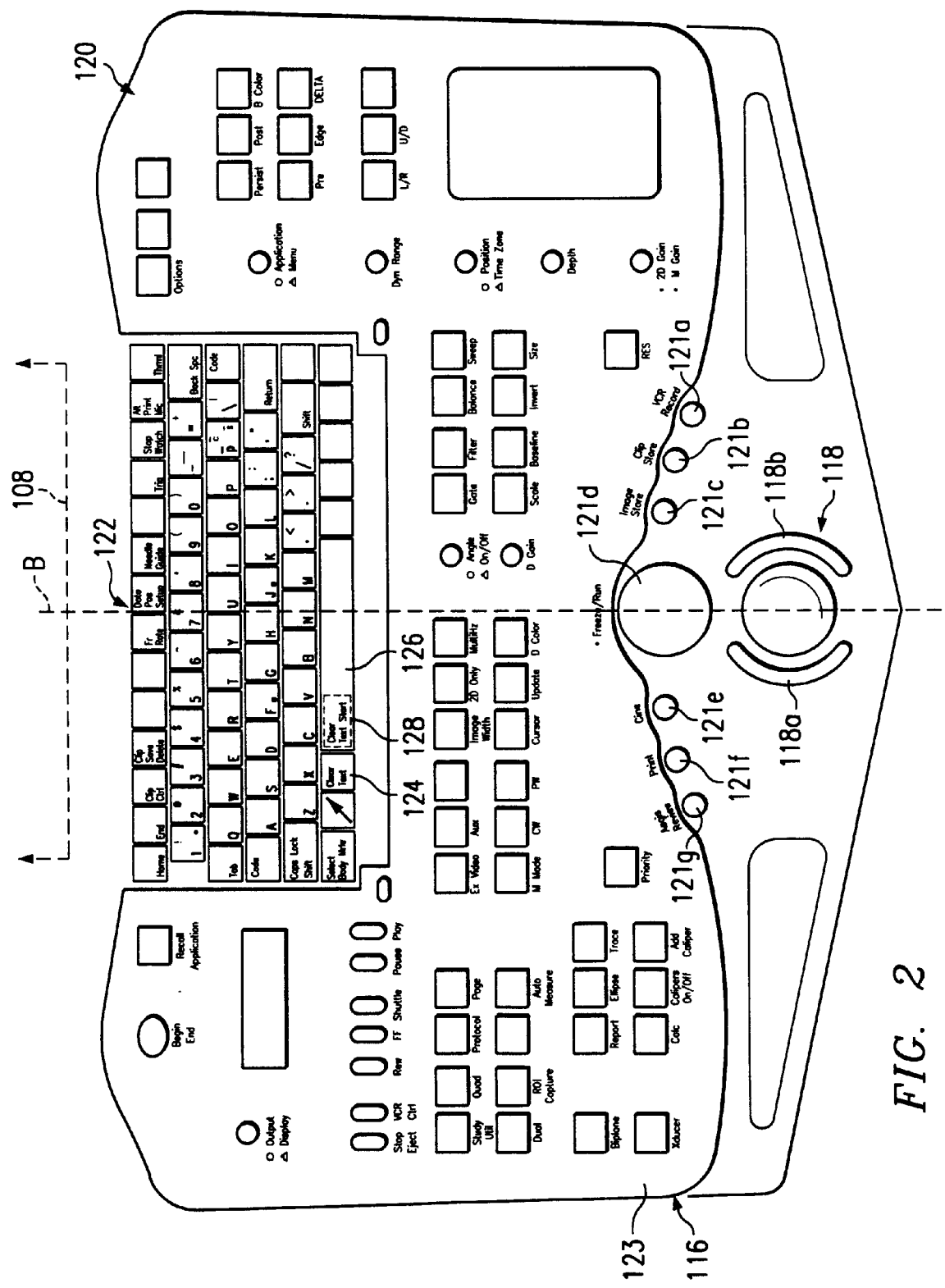
FIG. 2 is a schematic of an ultrasound input device of the present invention.

FIG. 2 is a schematic of the ultrasound input device 116, which as shown is structured to increase comfort and efficiency in its use by an operator. The console keys 120 include an alphanumeric device 122. To describe the position of the alphanumeric input device 122 with respect to an operator, the pointing device 118 is closest to the operator. On the opposing side of the input device 116 is the monitor 108, illustrated generally in phantom lines, and the keyboard is adjacent to the monitor 108. This spatial relationship allows the alphanumeric input device 122 to be readily available immediately above the pointing device 118 along a bilateral symmetry axis B. In this position, the alphanumeric input device 122 remains separate from the console key areas of the input device 116 designated for image capture and editing so that unintentional activation of the annotation function is avoided. Furthermore, the alphanumeric input device 122 is aligned with the pointing device As shown, the alphanumeric input device 122 is adjacent the position of the monitor 108. The alphanumeric input device 122 is an electromechanical device that provides character codes to the input/output ports of the computer 110 (see FIG. 1). The alphanumeric input device 122 can be provided by a QWERTY keyboard having a set of keys. The QWERTY keyboard layout is named for the six leftmost characters in the top row of alphabetic characters, and is a standard layout of most typewriters and computer keyboards. Other keyboard layouts, such as a Dvorak keyboard, can be used, but the QWERTY keyboard is preferable due to its general familiarity to operators. The alphanumeric input device 122 provides a character code that represents a particular character in a character set, for example, the ASCII ("American Standard Code for Information Interchange") character set, which is a standardized coding scheme that assigns numeric values to letters, numbers, punctuation marks, and other characters.

Character codes submitted by the alphanumeric input device 122 are received by the computer 110 (see FIG. 1). The computer 110 stores the character codes in a keyboard buffer, which is a portion of computer memory 114 (see FIG. 1) sufficient to store the most recently-typed characters. The alphanumeric input device 122 is used to annotate the ultrasound image 104 that is captured by the imaging system 102. The term "annotate" as used herein means an explanatory note or comment included with the image 104 to provide additional information. An annotation function enables an operator to annotate the image 104 electronically, identifying their comments with initials or other marks. The annotations made by an operator can also be performed through the pointing device 118.

The present invention invokes an annotation function in an ergonomically advantageous manner, and in a way that is intuitive to the operator. The term "invoke" as used herein means to call or to activate, and is used in reference to commands and subroutines.

Figure 3:
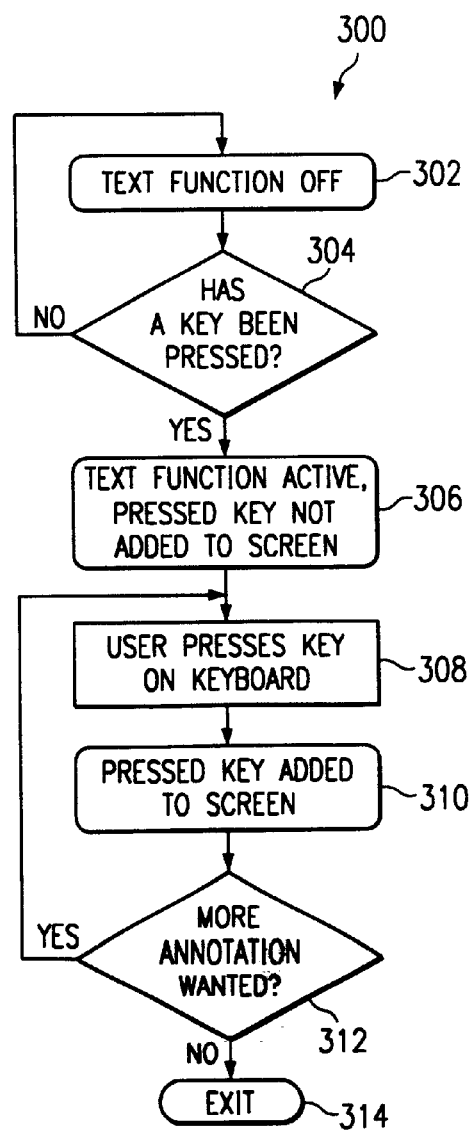
FIG. 3 is a flow chart that illustrates invoking the annotation function of the ultrasound system.

FIG. 3 is a flow chart that illustrates invoking the annotation function 300 of the ultrasound system 100. As necessary, FIG. 2 is referred to in the description of the flow chart of FIG. 3. The invocation routine described in FIG. 3 is preferably implemented in an object-oriented source computer code to provide ready upgradability and modular structure. Examples of an object-oriented computer language is C++. Preferably C++ is used to implement the invocation routine due to its flexibility and ready acceptance. The source computer code is reduced or compiled to an executable computer program format, which then can be executed on the computer 110 with the other resident programs, also known as "linking," in the ultrasound system 100.

The routine begins at the initial state 302 at which the annotation or text function is "OFF." The annotation function is "OFF" in the present system typically when there is no still-video image for annotating. For example, the annotation function is OFF, when there is video streaming from the imaging system 102 to the ultrasound system 100 for display on the monitor 108, or when reviewing electronically-stored records.

At step 304, the ultrasound system 100 polls the keyboard buffer at the times when its annotation function can be invoked. The annotation function can be invoked when there is a still-image 104 displayed on the screen 106 so that a record can be made of the image. If a character code has been received from the alphanumeric input device 122, indicating that a key has been pressed, then the annotation function is invoked at step 306. Otherwise, the routine returns to the initial state 302.

At step 308, routine 300, executed by the computer 110, waits for the operator to press a key. When a key is pressed and places another character code in the keyboard buffer, the routine annotates the image 104 with the character associated with the pressed key at step 310. The character is placed on the image at the last location of the on-screen cursor (as dictated by the pointing device 118) before the annotation function was invoked.

At step 312, the determination is made whether to continue adding annotations (characters) to the image 104 (see FIG. 1). If the operator has pressed the "TEXT" hard key 124 or has pressed another key to invoke another ultrasound function, then the annotation function 300 is exited at step 314. Otherwise, the routine 300 returns to step 300 to wait for the operator to press another key. The routine 300 continues until the "TEXT" hard key 124 or another function key is pressed.

It should be noted that any key of the alphanumeric input device 122 can be used to initiate the annotation function 300. Use of the space bar key 126, however, is preferred to invoke the function because it is the largest key of the standard QWERTY keyboard, and can readily accept a label 128, such as "Text Start," to indicate its annotation invocation function, as shown in FIG. 2. And by limiting activation of the annotation function 300 to a single QWERTY key, unintentional invocation of the annotation function 300 by the operator can be further minimized. The label 128 is preferably sized to be conspicuous to an operator, and can also be color-code to additionally recognizable and locatable by an operator.

Accordingly, the present invention provides an ultrasound system that is more intuitive as to invoking an annotation function to place comments on an image captured by the ultrasound system. Also, the positioning of the input device 122 avoids unintentional activation of the annotation function by placing the device apart from other graphic function keys used to capture and adjust images 104 captured by the ultrasound imaging system 102. Again, unintentional activation of the annotation function can be achieved by activating the function through a single key, and operator convenience is further emphasized by causing the function to be invoked through use of the space bar key of a QWERTY keyboard.

Although the invention has been described with reference to a specific embodiment, these descriptions are not meant to be construed in a limiting sense. Various modifications of the disclosed embodiments, as well as alternative embodiments of the invention will become apparent to persons skilled in the art upon reference to the description of the invention. It is therefore contemplated that the claims will cover any such modifications or embodiments that fall within the true scope and spirit of the invention.

What is claimed is:

1. A method for annotating an image captured by an ultrasound system, the method comprising the steps of:
   (a) pressing a key of an alphanumeric input device of the ultrasound system, the key including a label designating the key as an annotation function invocation key;
   (b) invoking an annotation function in response to a character code generated by said step of pressing the key;
   (c) pressing a second key of the alphanumeric input device of the ultrasound system; and
   (d) placing a character on the image in response to a second character code of the second key.

2. The method of claim 1 further comprising the step of:

(e) repeating steps (c) and (d) until an exit key is pressed.

3. The method of claim 1 wherein the alphanumeric input device is a QWERTY keyboard.

4. The method of claim 3 wherein the key is a space bar having a label designating the key as an annotation function invocation key.

5. The method of claim 1 wherein the alphanumeric input device is a Dvorak keyboard.

6. The method of claim 5 wherein the key is a space bar having a label designating the key as an annotation function invocation key.

7. The method of claim 1 wherein the character code is a code from an ASCII character code set.

8. The method of claim 1 wherein the character code is a space code.

9. The method of claim 8 wherein the second character code is a space code.

10. The method of claim 1 wherein the step of placing a character on the image further comprises the step of placing the character on the image at a screen position indicated by an on-screen cursor.

11. An apparatus for annotating an image captured by an ultrasound system, the apparatus comprising:

input means for invoking an annotation function executable on said ultrasound system in response to an operator command;

means for placing a character on the image in response to a further operator command; and means for exiting from said annotation function in response to an exit command of an operator.

12. The apparatus of claim 11 wherein the character is placed on the image at a screen position indicated by an on-screen cursor.

13. An input device of an ultrasound system for invoking an annotation function, the input device comprising:

a plurality of console keys for receiving input from an operator, said plurality of console keys including an alphanumeric input device for placing characters on an image captured by the ultrasound system; and an annotation function executable by the ultrasound system, the annotation function invoked by pressing a key of said alphanumeric device, the key including a label designating the key as an annotation function invocation key, said annotation function for placing a character on the image captured by the ultrasound system in response to a character code from said alphanumeric input device.

14. The input device of claim 13 further comprising:

a pointing device spaced apart from said alphanumeric device such that unintentional invocation of said annotation function is minimized.

15. The input device of claim 14 wherein said pointing device is spaced apart from said alphanumeric device along a bilateral symmetry axis of said alphanumeric input device.

16. The input device of claim 14 wherein said character is placed on said image at a screen position indicated by an on-screen cursor corresponding to said pointing device.

17. The input device of claim 14 wherein said pointing device is a track ball.

18. The input device of claim 13 wherein said alphanumeric input device is a QWERTY keyboard.

19. The input device of claim 13 wherein said key of said alphanumeric device is a space bar key having a label designating said key as an annotation function invocation key.

20. The input device of claim 13 wherein said character code is a code from an ASCII character code set.

* * * * *